United States Patent [19]

Gottlieb et al.

[11] 4,393,250

[45] Jul. 12, 1983

[54] PROCESS FOR PRODUCING ALCOHOLS AND ETHERS

[75] Inventors: Klaus Gottlieb, Herdecke-Ende; Hartmut Bruderreck, Gelsenkirchen-Buer; Friedel-Heinrich Wehmeier, Bottrop-Kirchhellen, all of Fed. Rep. of Germany

[73] Assignee: Veba Oel AG, Gelsenkirchen-Buer, Fed. Rep. of Germany

[21] Appl. No.: 372,804

[22] Filed: Apr. 28, 1982

[30] Foreign Application Priority Data

Apr. 28, 1981 [DE] Fed. Rep. of Germany ....... 3116779

[51] Int. Cl.³ .................... C07C 41/06; C07C 37/72
[52] U.S. Cl. .................................. 568/697; 568/918
[58] Field of Search ........................... 568/697, 918

[56] References Cited

U.S. PATENT DOCUMENTS 3,119,766  1/1964  Voltz et al. ................. 568/697
3,726,942  4/1973  Louder ....................... 568/697
3,912,463 10/1975  Kozlowski et al. .......... 568/697
4,252,541  2/1981  Herbstman .................. 568/697
4,329,516  5/1982  Al-Muddarris .............. 568/697

FOREIGN PATENT DOCUMENTS 2040924  9/1980  United Kingdom ............ 568/697
2080297  7/1981  United Kingdom ............ 568/697

Primary Examiner—J. E. Evans

Attorney, Agent, or Firm—Oblon, Fisher, Spivak, McClelland & Maier

[57] ABSTRACT

A process for producing isopropyl alcohol and isopropyl tert-butyl ether from a mixture of light hydrocarbons containing propane and butane, comprises:
(a) separating from the mixture of light hydrocarbons a propane fraction and a butane fraction containing at least n-butane;
(b) isomerizing at least a portion of the n-butane in the butane fraction from step (a) whereby a hydrocarbon mixture containing at least n-butane and isobutane is formed;
(c) catalytically dehydrogenating the isobutane in the hydrocarbon mixture from step (b) whereby a hydrocarbon mixture containing at least isobutene is produced;
(d) catalytically dehydrogenating the propane in the propane fraction from step (a) whereby a hydrocarbon mixture containing at least propene is produced;
(e) reacting the propene in the hydrocarbon mixture from step (d) with water, whereby a mixture containing hydrocarbons and isopropyl alcohol is formed;
(f) reacting the isopropyl alcohol from step (e) with at least part of the isobutene in the hydrocarbon mixture from step (c) whereby a mixture containing hydrocarbons and isopropyl tert-butyl ether is formed;
(g) recycling the hydrocarbons in the hydrocarbon mixture from step (e) to step (d), respectively;
(h) recycling the hydrocarbons in the hydrocarbon mixture from step (f) to step (c); and
(i) recovering at least the isopropyl tert-butyl ether.

23 Claims, 1 Drawing Figure

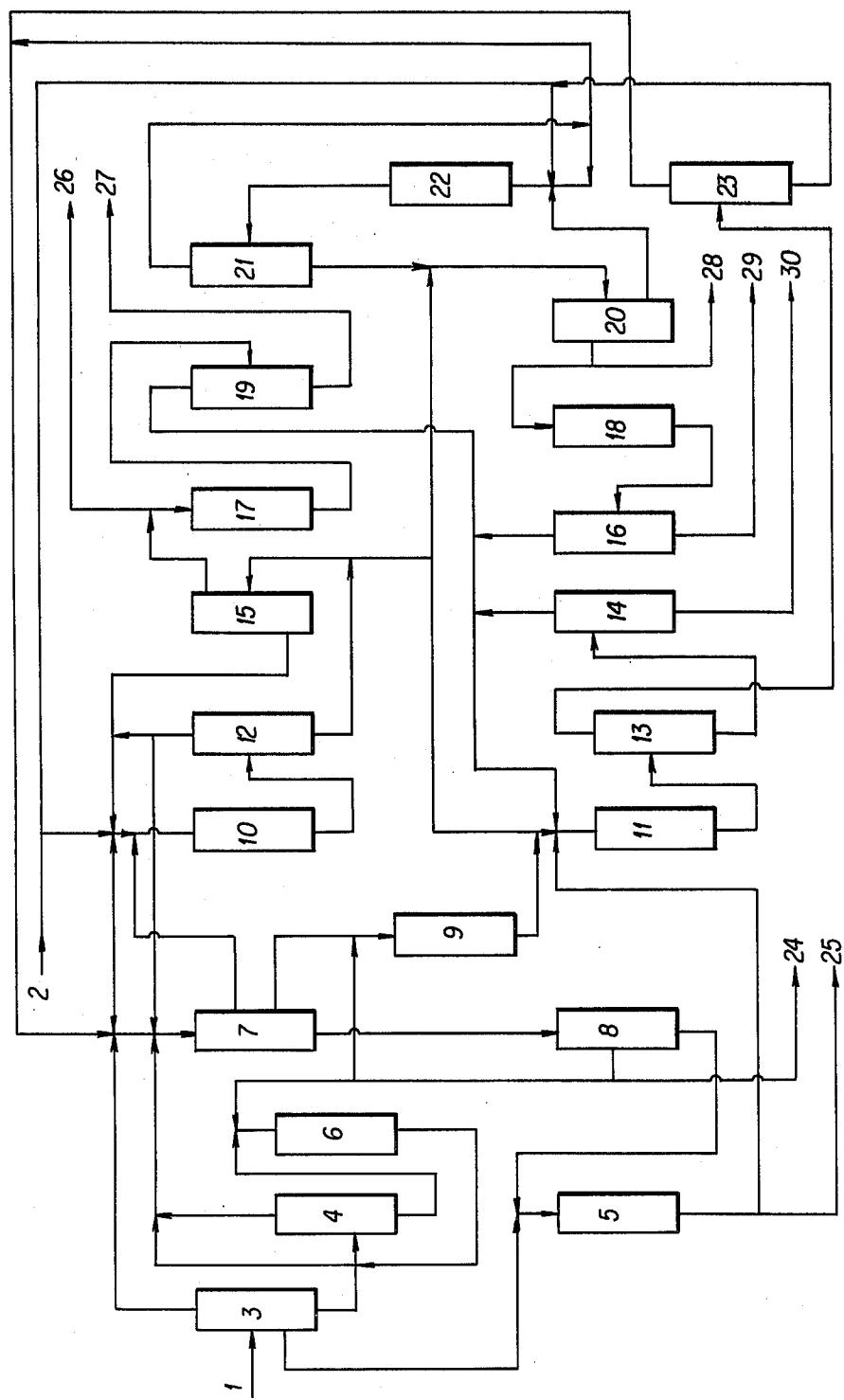

PROCESS FOR PRODUCING ALCOHOLS AND ETHERS

BACKGROUND OF THE INVENTION

1. Field of the Invention

This invention relates to a process for producing alcohols and ethers from hydrocarbons which are gaseous under normal conditions, e.g., such as those occurring during crude oil production or refining. Collecting, purifying and transporting these paraffin hydrocarbons is very difficult and costly, and as a result even frequently rather large volumes of gas are flared. The present invention, therefore, pertains to converting, on the spot, these gaseous, light hydrocarbons formed during petroleum refining into valuable products whose long distance transport presents fewer difficulties than transporting the gaseous hydrocarbons.

2. Description of the Prior Art

It is known from German OS Nos. 26 20 011 and 29 21 576 to convert butane into methyl tert-butyl ether. In this process n-butane is partially or completely isomerized into isobutane (2-methylpropane) and the n-butane-isobutane mixture is dehydrogenated thus forming n-butenes in addition to isobutene. The dehydrogenation reaction mixture is then etherified with excess methyl alcohol, whereby the isobutene formed in the dehydrogenation step is converted into methyl tert-butyl ether. The excess methyl alcohol from the etherification reaction mixture is removed either with water or by azeotropic distillation.

SUMMARY OF THE INVENTION

The present invention, on the other hand, proceeds by converting the propane as well as possibly the n-butenes formed in the dehydrogenation of n-butane to $C_3$- and $C_4$-alcohols and with isobutene into the ethers derived from $C_3$- and $C_4$-alcohols, whereby a portion of the isobutene can also be converted with methyl alcohol, produced from methane and ethane, into methyl tert-butyl ether in a known manner.

To this end, according to the present invention, a propane and a butane fraction are separated from the mixture of lighter hydrocarbons containing propane and butane. Propane is catalytically dehydrogenated and the resulting propene is converted with water into isopropyl alcohol (propane-2-ol). In the butane fraction n-butane is isomerized, catalytically dehydrogenated and the isobutene contained in the dehydrogenation reaction mixture is converted with at least a part of the isopropyl alcohol recovered from the propane fraction into isopropyl tert-butyl ether. The unconverted hydrocarbons from the propene hydration as well as unconverted isobutane from the etherification are recycled to the dehydrogenation step.

According to a further feature of the invention sec-butyl alcohol (butane-2-ol) and sec-butyl tert-butyl ether are recovered from the mixture of lighter hydrocarbons in addition to isopropyl alcohol and isopropyl tert-butyl ether. To do this only a part of the n-butane is isomerized, butadiene in the dehydrogenation reaction mixture is selectively hydrogenated while simultaneously converting butene-1 to butene-2, and a part of the isobutene contained in the dehydrogenation reaction mixture is converted with recycled sec-butyl alcohol into sec-butyl tert-butyl ether, while another part of the isobutene, as described above, is converted with isopropyl alcohol into isopropyl tert-butyl ether. The sec-butyl alcohol is produced by reaction of water with the butene-2 of the hydrocarbon mixture, which contains predominantly butene-2 and butane, after the etherification.

The invention also makes it possible to recover tert-butyl-alcohol (2-methylpropan-2-ol), particularly in a mixture with isopropyl alcohol and isopropyl tert-butyl ether and/or sec-butyl alcohol and sec-butyl tert-butyl ether from the alcohols and isobutene containing water.

Finally the present invention also makes it possible to recover methyl alcohol and methyl tert-butyl ether in addition to the alcohols and ethers mentioned above. To this end a fraction of the hydrocarbon mixture used as the raw material containing methane and ethane is separated in addition to the propane and butane fractions and is combined with the stream of methane, ethane and ethene occurring in the dehydrogenation of butane and propane. From this mixture methyl alcohol is produced by catalytic reformation with steam, for example, under a pressure of 40–100 bar and at temperatures of 210°–300° C. in a known manner, and this is converted with a portion of the isobutene contained in the dehydrogenation reaction mixture into methyl tert-butyl ether.

BRIEF DESCRIPTION OF THE DRAWINGS

Further features of the invention will be revealed in the following description of the process in which the process is described in greater detail with reference to the flow chart found in the accompanying drawing. The chart illustrates a preferred embodiment of the method according to the present invention. Parts that are not necessary for an understanding of the principle, such as pumps, heat exchangers, some distillation columns and the like, are omitted.

DESCRIPTION OF THE PREFERRED EMBODIMENTS

The hydrocarbon mixture 1 is separated by distillation 3 into a fraction containing butane, a fraction containing propane and a fraction containing ethane and methane. Isomerization 6, n-butane to isobutane, takes place in a known manner on a platinum-containing fixed bed catalyst in the presence of hydrogen at temperatures of 150°–210° C. and pressures of 15–30 bar. The pressure and temperature reaction conditions are controlled together so that the isomerization equilibrium is attained as far as possible.

Hydrogen and methane, ethane and propane produced during the isomerization are separated from the reaction mixture leaving the isomerization reactor 6 and containing up to more than 50% of isobutane. The $C_4$-isomerizate is combined with the added butane fraction. An aliquot portion of the isobutane-n-butane mixture is rectified in a distillation column 4 with 30–100 plates under pressure of 7–14 bar and at temperatures of 40°–80° C., so that the isobutane-n-butane mixture withdrawn overhead has an isobutane content of 80–98%. The n-butane removed from the bottom of the distillation column 4 is recycled to the isomerization 6. The overhead product from the distillation column 4 is combined with the remaining $C_4$-isomerizate and the remaining portion of the butane fraction used and fed to the dehydrogenation 7 along with the isobutane recycled from the etherifications 11, 17 and 18 and the hydrocarbons recycled from the hydration 22.

Through isomerization and distillation n-butane is converted into isobutane in such an amount as is necessary as the predetermined stoichiometric amount for the etherification of the total amount of alcohol produced. The isobutane content of the butane stream after isomerization and distillation is 40–98% by weight, preferably 55–98% by weight.

The propane stream can be combined with the propane recycled from the hydration 10 and taken to a separate dehydrogenation stage. In the preferred embodiment of the method according to the invention the propane fraction is combined with the hydrocarbons recycled from the hydration 10 and taken to the common dehydrogenation 7 together with the butane feed produced according to the invention.

The dehydrogenation of the $C_4$- and $C_3$-hydrocarbons is carried out catalytically by a conventional procedure, either in a fixed bed or a fluidized bed reactor. The dehydrogenation temperature is between 530° and 700° C., the pressure between 0.2 and 5 bar, preferably between 0.3 and 1.5 bar. The dehydrogenation catalysts consist generally of active aluminum oxide and additives of chromium oxide or platinum, which are applied by impregnation to $Al_2O_3$.

The coke produced during the reaction phase is burned off with air in a regeneration phase; the liberated heat is recovered for use as process heat. The dehydrogenation reaction mixtures are divided by cooling and compression into a gaseous stream containing predominantly methane, ethane, ethylene and hydrogen, and liquid streams containing predominantly propane and propene or respectively butanes, butadiene and butenes.

The hydrogen is removed to large extent from the gaseous stream in the purifying unit 8 by a conventional process. Methane, ethane, ethene and residual hydrogen together with the fraction containing methane and ethane are taken to the methyl alcohol production unit 5. When there is no adequate use for the total amount of hydrogen, only as much of the hydrogen is removed from the reaction mixture fraction containing methane and ethane after dehydrogenation as is needed for the isomerization and hydrogenation reactions. The remaining hydrogen can be removed with the dehydrogenation exhaust gas at 24 for use in the generation of process energy.

If, according to a special embodiment of the method according to the invention, there is a common dehydrogenation 7 of propane and butane, the dehydrogenation reaction mixture containing the $C_3$- and $C_4$-hydrocarbons is separated in a rectification column into a stream containing propane and propene and a stream containing predominantly butanes, butenes and butadiene.

The stream containing all $C_4$-hydrocarbons is taken to a selective hydrogenation 9 and hydroisomerization, where butadiene is selectively hydrogenated into butene and all butene-1 is simultaneously converted into butene-2. Selective hydrogenation and hydroisomerization are carried out in a known manner, i.e., catalytically in the presence of hydrogen in a fixed bed reactor. The temperature is 20°–80° C. preferably 30°–60° C., the pressure 1–20 bar, preferably 1.5–10 bar. The catalyst used here consists generally of a carrier, e.g. aluminum oxide or silicon dioxide and additives of platinum, palladium or nickel.

The hydrogen concentration and the feed rate are chosen so that butadiene is nearly completely (residual butadiene content in the reaction mixture less than 0.5% by weight) converted into butene-2, and butene-1 is converted into butene-2 with maximum yield near the thermodynamic equilibrium value, so that the smallest possible amount (less than 10% by weight) of butenes is hydrogenated into n-butane.

The purpose of this step is to allow isobutane to be separated by distillation after etherification, so that butene and n-butane remain in the sump of the column. The boiling point difference between isobutane on the one hand, and n-butane and butene-2 on the other hand is so great that it is possible to carry out a simple distillative separation of isobutane if butene-1 is previously converted by hydroisomerization into butene-2 and isobutene is separated by etherification. In a special embodiment of the process of the invention, the selective hydrogenation and hydroisomerization are placed after the etherification; this is preferable if the butadiene content of the $C_4$-fraction is less than 2% by weight, since in this case polymer materials formed in small quantities from butadiene cause no disruption of the etherification.

If, according to the method according to the invention, only isopropyl tert-butyl ether, or possibly also methyl tert-butyl ether are to be produced, the butene and butadiene content is adjusted to be so low that selective hydrogenation and hydroisomerization are rendered superfluous.

The $C_3$-fraction containing propene removed from the dehydrogenation mixture is taken to the hydration reactor 10 where isopropyl alcohol is catalytically synthesized from propene and water 2 under a pressure of 30–100 bar, preferably 40–80 bar and at temperatures of 100°–170° C., preferably 130°–160° C. Acidic catalysts are used, preferably strongly acidic cation exchangers consisting of sulfonated polystyrene resins cross-linked with divinyl benzene.

In the feed stream 1–20 moles of water, preferably 3–8 moles are used per 1 mole of propene. The space velocity in liters of feed per liter of catalyst per hour is 0.3–25, preferably 0.5–10. Under these reaction conditions 10–70% of the propene used is converted to isopropyl alcohol and di-isopropyl ether.

The $C_3$-hydrocarbons are removed by distillation from the final reaction mixture as overhead in the distillation tower 12 a partial stream is recycled back into the hydration reactor 10 and a quantitatively smaller portion is recycled back to the dehydrogenation. The isopropyl alcohol-water mixture in the water wash can be combined with the isopropyl alcohol-water mixture formed in the etherification. This then may be mixed, after isopropyl alcohol enrichment by distillation, with an organic solvent which is suitable as an extraction medium for isopropyl alcohol, is immiscible with water and is easily separated from isopropyl alcohol. It is a particular feature of this invention that the olefin-containing $C_3$- or especially the $C_4$-streams produced in the process are used for this.

After dividing the extraction mixture into an organic phase and an aqueous phase, the organic phase contains 40–95% of the resulting amount of isopropyl alcohol and 80–98% of the amount of di-isopropyl ether. The hydrocarbons are removed from the organic phase by distillation and recycled to the extraction 15. The isopropyl alcohol removed from the sump is taken, along with the di-isopropyl ether produced, to the etherification 17.

In the preferred embodiment the $C_4$-fraction containing isobutene is used for the extraction 15. To accomplish this, one part by weight of the water-isopropyl alcohol mixture withdrawn from the bottom of the column 12 is mixed with 1-20 parts by weight of the C$_4$-fraction and this is taken to the extraction step 15 where the total mixture is separated into an aqueous and an organic phase. The organic phase contains 20-60% by weight of the isopropyl alcohol taken to the extraction and small amounts of water; from this a part of the C$_4$-fraction containing isobutene is removed by distillation, so that in addition to a little water the residue contains isobutene and isopropyl alcohol in the stoichiometric ratio needed for the etherification 17. If, in addition to isopropyl tert-butyl ether, isopropyl alcohol is also to be produced, the organic phase is completely separated by distillation into isopropyl alcohol and the C$_4$-fraction containing isobutene and isopropyl alcohol is withdrawn from the bottom of the rectifier column at 26. The etherification to produce isopropyl tert-butyl ether is fed in this case with separate streams for isopropyl alcohol and the C$_4$-fration containing isobutene. The isopropyl alcohol-depleted aqueous phase is recycled to the hydration 10.

In order to increase the separation performance of the extraction stage, the isopropyl alcohol-water mixture withdrawn from the bottom of column 12 can first be separated by distillation into an isopropyl alcohol-enriched isopropyl alcohol-water mixture and then treated, as mentioned above, with the C$_4$-fraction containing isobutene. The degree of enrichment can run to 88% by weight. For extractively separating isopropyl alcohol, one part by weight of the isopropanol-enriched aqueous mixture is mixed with 1-5 parts by weight of the C$_4$-fraction containing isobutene and is taken to the extraction step 15 where 70-95% by weight of the organic phase containing isopropyl alcohol formed during hydration is separated. The water is returned to hydration.

In a special embodiment of the process according to the invention an isopropyl alcohol-water mixture can be withdrawn from the top of the enrichment tower after the hydration 10 and taken directly to the etherification 17 and an ether-alcohol mixture containing tert-butyl-alcohol can be prepared and drawn off at 27.

Isobutene and isopropyl alcohol are catalytically etherified whereby 10-100%, preferably 50-90% of the isopropyl alcohol is converted to form isopropyl tert-butyl ether as well as small amounts of di-isopropyl ether. Small amounts of tert-butyl alcohol and trimethylpentenes are also formed. It was found that n-butenes undergo no reaction and leave the etherification reactor 17 unchanged. Sulfonated cation exchanger resins serve as acidic catalysts; again, those preferred are strongly acidic ion exchangers based on sulfonated styrene crosslinked with divinyl benzene. Etherification takes place in the liquid phase in a single or multi-staged fixed bed reactor 17 at temperatures between 20°-150° C. preferably at 30°-60° C. and under pressures sufficient to liquify the isobutene, namely 4-40 bar, preferably 8-16 bar. The molar ratio of isopropanol to isobutene should be in the range of 1:0.5 to 1:10, preferably 1:1 to 1:3, the space velocity, expressed in liters of feed per liter of catalyst per hour, in the range of 0.3-50, preferably 1-20. The stream leaving the etherification reactor 17 consists predominantly of isopropyl tert-butyl ether, unconverted isobutene, isopropyl alcohol and possibly butene and butane.

In order to separate the isopropyl tert-butyl ether the mixture is taken to a pressure distillation column 19. The total conversion of isobutene can be increased by recycling the C$_4$-hydrocarbons containing the unconverted isobutene into the isopropyl alcohol etherification 17. If methyl tert-butyl ether is also produced in the selected embodiment by etherification with methyl alcohol, it is advantageous to take the unconverted C$_4$-hydrocarbons containing isobutene to the methyl alcohol etherification 11.

The ether-alcohol mixture from the bottom of the column 19 can be separated into a water-alcohol phase and an ether phase by water washing. For this purpose, 1-20 parts by weight of water, preferably 5-10 parts by weight of water, are added to one part by weight of ether-alcohol mixture and the total mixture is vigorously mixed at 15°-50° C., preferably 20°-40° C. Separation into an ether phase and a water-alcohol phase can be carried out by the mixer-settler principle, for example. The separated ether raffinate contains 0.5-3% by weight of trimethylpentenes and respectively less than 1% by weight of isopropyl alcohol, 1% by weight of isobutene, 0.5% by weight of tert-butyl alcohol and 0.2% by weight of water.

The water needed for the water wash is composed of a component from the recycle water of the extraction 15 and another from the fresh water 2 needed for hydration. The water phase containing isopropyl alcohol withdrawn from the water wash can be returned to the extraction 15 and be processed as described above with the reaction mixture from the hydration reactor 10.

If, according to the preferred embodiment, an ether-isopropyl alcohol mixture is to be produced, isopropyl alcohol is etherified with such an excess of isobutene that the separation of the unconverted alcohol is rendered superfluous. In that case an ether-alcohol mixture is withdrawn from the bottom of the pressure column 19 at 27.

The preparation of isopropyl tert-butyl ether is known from German OS Nos. 25 35 471 and 26 20 011, U.S. Pat. No. 4,046,520 and Canadian Pat. No. 958,213. In contrast to the embodiments described there, which all rely on an excess of isopropyl alcohol during the reaction and higher temperatures, in the present preferred embodiment the process is carried out with an excess of isobutene and lower temperatures, in order to achieve the highest possible isopropyl alcohol conversion and thus possibly to be able to eliminate the separation and recycling of the unconverted alcohol. Even for the embodiment described above in which the unconverted isopropyl alcohol is separated by water treatment and returned to the hydration, it is more economical to operate with an excess of isobutene and the highest possible isopropyl alcohol conversion.

In a special embodiment of the method according to the invention, the C$_4$-fraction containing isobutene is reacted with an isopropyl alcohol-water mixture in the presence of the acidic catalysts already described, whereby 10-95%, preferably 50-90% of the isopropyl alcohol reacts with isobutene, to form isopropyl tert-butyl ether, and water reacts 80-100% with isobutene, forming tert-butyl alcohol. The isopropyl alcohol-water mixture used as feed can contain 1-50% by weight of water; in particular, an alcohol-water mixture formed in an azeotropic distillation, e.g., that formed in the isopropyl alcohol enrichment process described above, can be used.

It was found that even in the presence of water the n-butenes undergo no reaction. Surprisingly, it was also determined that tert-butyl alcohol forms no reaction product through parallel reaction with isobutene. The same sulfonated, strongly acidic ion exchangers can be used as catalysts as were used in the previously described embodiment. Etherification occurs in a multi-staged fixed bed reactor at temperatures between 20° and 150° C., preferably at 30°–80° C. and pressures adequate to liquify isobutene, that is, 4–40 bar, preferably 8–16 bar. The molar ratio of isopropyl alcohol to isobutene is in the range of 0.1:1 to 1:10, preferably 1:0.7 to 1:5, the molar ratio of water to isobutene is in the range of 1:1 to 1:20, preferably 1:1.5 to 1:10; the space velocity in liters of feed per liter of catalyst per hour is in the range of 0.3–50, preferably 1–20. By distillation under pressure the ether-alcohol mixture is separated from the unconverted hydrocarbons, which are then recycled, as was described in the previous embodiment of etherification of isopropyl alcohol without added water.

An additional stream of the $C_4$-fraction containing isobutene is catalytically etherified 18 with sec-butanol, whereby 10–100%, preferably 50–90% of the sec-butanol is reacted to form sec-butyl tert-butyl ether. The n-butenes undergo no reaction and leave the reactor 18 unchanged.

Known acidic cation exchanger resins are used as catalysts, again the most preferred are sulfonated polystyrene resins cross-linked with divinyl benzene. Etherification in the liquid phase takes place in a single or multi-staged fixed bed reactor at temperatures between 20° and 150° C., preferably at 30°–60° C. and under pressures adequate to liquify isobutene, namely 4–40 bar, preferably 8–16 bar. The molar ratio of isobutene to sec-butyl alcohol should be in the range of 0.5:1 to 10:1, preferably from 1:1 to 3:1, the space velocity, expressed in liters of feed per liter of catalyst per hour, in the range of 0.3 to 50, preferably 1 to 20.

The stream leaving the etherification reactor 18 consists essentially of sec-butyl tert-butyl ether, unconverted sec-butyl alcohol, isobutane, isobutene, n-butane and butenes. The mixture is taken to a pressure distillation column 16 in order to separate the sec-butyl tert-butyl ether. The $C_4$-hydrocarbons containing unconverted isobutene are withdrawn overhead and are taken to the sec-butyl alcohol etherification 18 or possibly to the methyl alcohol etherification 11 in order to increase the total conversion of isobutene. The ether-alcohol mixture from the bottom of column 16 can be separated into a water-alcohol phase and an ether phase as was already described in relation to the production of isopropyl tert-butyl ether, possibly by washing with water. In this procedure 1 to 20, preferably 5 to 10 parts by weight of water are added to one part by weight of the ether-alcohol mixture and the total mixture is vigorously mixed at 15° to 50° C., preferably 20° to 40° C. The separated ether raffinate contains 0.5–5% by weight of trimethylpentenes, and respectively less than 1% by weight of isobutene, 2% by weight of sec-butyl alcohol, 0.5% by weight of tert-butyl alcohol and 0.2% by weight of water. The water needed for the water wash is made up in part of recycled water from the extraction 20 and in part of the fresh water 2 needed for the hydration 22 of butene. The alcohol-containing water phase withdrawn from the water wash is returned to the hydration 22 and processed together with the reaction mixture from the hydration reactor.

If, according to the preferred embodiment, an ether-alcohol mixture is to be produced, etherification is carried out with such an excess of isobutene that the separation of unconverted sec-butyl alcohol can be eliminated. In that case an ether-alcohol mixture is withdrawn from the bottom of the pressure column 16 at 29.

In a special embodiment of the method according to the invention, the $C_4$-stream containing isobutene is catalytically etherified with a sec-butyl alcohol-water mixture, whereby 1–95%, preferably 50–90% of the sec-butyl alcohol is converted to sec-butyl tert-butyl ether and 50–100% of the water is reacted to form tert-butyl alcohol. The sec-butyl alcohol-water mixture used as feed can contain 1 to 50% by weight of water, in particular one can use a sec-butyl alcohol-water mixture produced during an azeotropic distillation.

It has been found that even in the presence of water the n-butenes undergo no reaction during etherification. The strongly acidic ion exchanger resins mentioned above can be used as catalysts, for example. Again, the most preferred are sulfonated polystyrene resins that are cross-linked with divinyl benzene. The reaction occurs in a single or multi-staged fixed bed reactor at temperatures between 20° and 150° C., preferably at 30° to 80° C. and under pressures adequate to liquify isobutene, namely 4 to 40 bar, preferably 8 to 16 bar. The molar ratio of sec-butyl alcohol to isobutene is in the range of 1:0.1 to 1:10, preferably from 1:0.7 to 1:5; the molar ratio of water to isobutene is in the range of 1:1 to 1:20, preferably from 1:1.5 to 1:10; the space velocity in liters of feed per liter of catalyst per hour is in the range of 0.3 to 50, preferably 1 to 20.

The ether-alcohol mixture is separated by pressure distillation from the unconverted hydrocarbons still containing isobutene, which may be added or recycled to the etherification step 18 or methyl alcohol-etherification 11 in order to achieve a higher total conversion.

In another special embodiment of the method according to the invention mixtures containing isopropyl-tert-butyl ether, sec-butyl tert-butyl ether and alcohols can be produced by common etherification of mixtures containing isopropyl alcohol, sec-butyl alcohol and possibly water with isobutene or a $C_4$-fraction containing isobutene. Surprisingly, it has been found that the reaction rates of both etherification reactions are approximately equal. This makes it possible to produce ether mixtures in one step. The reaction conditions and the particulars of the process are the same as those described above regarding the embodiments of separated etherification of isopropyl alcohol and sec-butyl alcohol or the corresponding alcohol-water mixture with isobutene.

To etherify sec-butyl alcohol-isopropyl alcohol mixtures the molar ratio of isobutene to the total amount of alcohol is selected to be 0.5:1 to 10:1, preferably 1:1 to 3:1, the temperature 20° to 150° C., preferably 30° to 60° C., the pressure 4 to 40 bar, preferably 8 to 16 bar. The space velocity, expressed in liters of feed per liter of catalyst per hour, is 0.3 to 50, preferably 1 to 20. In the etherification of sec-butyl alcohol-isopropyl alcohol-water mixtures the molar ratio of isobutene to the total amount of alcohol is 0.1:1 to 10:1, preferably 0.7:1 to 5:1, the molar ratio of water to isobutene 1:1 to 1:20, preferably 1:1.5 to 1:10, the temperature of 20° to 150° C., preferably 30° to 80° C., the pressure 4 to 40 bar, preferably 8 to 16 bar. The space velocity, expressed in liters of feed per liter of catalyst per hour, is in the range of 0.3 to 50, preferably 1 to 20. As catalysts for the etherification of the alcohol mixture as well as the alcohol-water mixture the acidic ion exchanger resins already mentioned above are used.

Another partial stream of the C4-fraction containing isobutene may be combined with the C4-hydrocarbon output streams from the etherification 17,18 of isopropyl alcohol and sec-butyl alcohol, and the isobutene contained in them catalytically etherified with methyl alcohol, whereby the isobutene is nearly quantitatively converted into methyl tert-butyl ether. The sulfonated, strongly acidic ion exchange resins already described above can be generally used as catalysts. The etherification also takes place in the liquid phase in a fixed bed reactor 11. The temperatures are in the range of 30° to 100° C. preferably 60° to 90° C., the pressures 4 to 24 bar, preferably 10 to 20 bar. Excess methyl alcohol is used in the etherification in order to convert as much isobutene as possible. The molar ratio of methyl alcohol to isobutene is generally in the range of 1:1 to 2:1, preferably in the range of 1.1:1 to 1.5:1. The stream leaving the etherification reactor 11 consists essentially of methyl tert-butyl ether, isobutane, n-butane, butenes and methyl alcohol.

To remove the methyl tert-butyl ether the mixture is taken to a pressure distillation column 13 in which the unconverted C4-hydrocarbons, n-butane, isobutene and butenes are withdrawn as overhead and sent to a second distillation column 23 where isobutene is separated from the remaining C4-hydrocarbons, n-butane and butene. Isobutane is recycled to the dehydrogenation 7; the n-butane and butene fraction withdrawn from the bottom is taken to the butene hydration 22. The methyl alcohol-ether mixture withdrawn from the bottom of the first rectifier tower 13 is distilled in another pressure distillation column 14, whereby an ether-methyl alcohol-azeotrope is the overhead and is recycled to the etherification 11, while methyl tert-butyl ether is withdrawn at 30 from the bottom. Here, too, it is unnecessary to distill to pure methyl tert-butyl ether if an alcohol-ether mixture is to be produced.

According to the preferred embodiment of the method according to the invention the C4-hydrocarbon mixture containing isobutene is etherified with methyl alcohol which was produced by reforming light hydrocarbons with steam and by catalytic synthesis under a pressure of 40 to 100 bar, at temperatures of 200°-300° C. The fraction of the light hydrocarbons containing methane and ethane occurring in the production and refining of crude oil is used for the methyl alcohol synthesis. If it is intended to recover methyl alcohol in the process, it is withdrawn at 25.

The C4-fraction separated after the methyl alcohol etherification and containing only n-butene and n-butane is taken to the butene hydration 22, where sec-butyl alcohol is produced by catalytic synthesis from butene and water at a pressure of 20 to 80 bar and 100°-170° C., preferably at 30 to 60 bar and 120°-160° C. The same strongly acidic ion exchangers are used as catalysts as were used in the hydration of propene. In the feed stream 2-10 moles, preferably 3-6 moles of water are used per 1 mole of butene. The space velocity in liters of feed per liter of catalyst per hour is 0.2-15, preferably 0.5-5. Under these reaction conditions 5-35% of the n-butene used is reacted to form sec-butyl alcohol and traces of di-sec butyl ether. The C4-hydrocarbons are removed by distillation from the reaction mixture as overhead in the column 21 and a partial stream is recycled to the hydration reactor 22, a smaller portion to the dehydrogenation 7. The sec-butyl alcohol-water mixture, which may be combined with the sec-butyl alcohol-water mixture produced in the water wash of the etherification 18, may be mixed with an organic solvent after being enriched in sec-butyl alcohol by distillation. The organic solvent is suitable as an extraction medium for sec-butyl alcohol, is immiscible with water and is easily separated from sec-butyl alcohol. According to a special embodiment of this invention one of the C4-streams containing n-butene or isobutene produced in the process is used for this. After separating the extraction mixture into an organic phase and an aqueous phase, the organic phase contains 50-98% of the amount of sec-butyl alcohol produced and 90-98% of the di-sec-butyl ether. The C4-hydrocarbons are separated from the organic phase by distillation are recycled to the extraction stage 20. The sec-butyl alcohol removed from the bottom of the distillation is taken to the etherification 18 along with the di-sec-butyl ether that is produced.

In the preferred embodiment the C4-fraction containing isobutene is used for extraction 20. For this purpose, 1 part by weight of the water-sec-butyl alcohol mixture withdrawn from the bottom of the tower 21 is mixed with 2-10 parts by weight of the C4-fraction and taken to the extraction stage 20 where the total mixture is separated into an aqueous and an organic phase. The organic phase contains 50-80% by weight of the sec-butyl alcohol sent to the extraction and small amounts of water. By distillation a mixture containing small amounts of water is separated from the C4-fraction containing sec-butyl alcohol and isobutene. The mixture contains isobutene and sec-butyl alcohol in the necessary stoichiometric amounts for etherification 18. If, in addition to sec-butyl tert-butyl ether, sec-butyl alcohol is also to be produced, the organic phase is completely separated by distillation into sec-butyl alcohol and the C4-fraction containing isobutene and sec-butyl alcohol is withdrawn from the bottom of the rectification tower at 28. In this case the etherification for producing sec-butyl tert-butyl ether is fed with separate streams of sec-butyl alcohol and the C4-fraction containing isobutene. The aqueous phase that was separated in extraction and is depleted in sec-butyl alcohol is recycled into the hydration 22.

To increase the separating capacity of the extraction stage, a sec-butyl alcohol-water mixture enriched in sec-butyl alcohol can first be separated by distillation from the sec-butyl alcohol-water mixture drawn off from the bottom of column 21, and as described above, treated with the C4-fraction containing isobutene. The degree of enrichment can amount to 80% by weight. To separate sec-butyl alcohol by extraction, 1 part by weight of the sec-butyl alcohol-enriched aqueous mixture is mixed with 0.5-5 parts by weight of C4-fraction containing isobutene and taken to the extraction stage 20 where an organic phase containing 80-98% by weight of the sec-butyl alcohol formed in the hydration is separated. Water is recycled to the hydration. Instead of the C4-fraction containing isobutene, the isobutene-free C4-fraction from the input of the butene hydration 22, containing butene-2 and n-butane, can also be used as the extraction medium.

Finally, in another embodiment of the method according to the invention, a sec-butyl alcohol-water mixture withdrawn from the top of an enrichment column after the hydration 22 can be taken directly to etherification 18 and an ether-alcohol mixture containing tert-butyl alcohol can be produced, which can be drawn off at 29.

Having now generally described the invention, a further understanding may be obtained by reference to the following illustrative examples, which are included herein only for the purposes of illustration and are not intended to be limiting unless so specified.

EXAMPLE 1

Isobutene and isopropyl alcohol were reacted in a molar ratio of 1.3:1 at a temperature of 60° C. and a pressure above the vapor pressure of isobutene so that the latter was present as a liquid, namely 16 bar. A slender tube reactor with an interior diameter to length ratio of 1:30 was used as the reactor and a strongly acidic ion exchanger resin (commercial product Lewawit SPC 118) was used as the catalyst. The reactor, filled with catalyst, was fed with 2.2 parts by weight of the specified isopropyl alcohol-isobutene mixture per hour per part by weight of dry catalyst. A suitable pre-heater was used to establish the specified temperature; the heat liberated during the reaction was removed by a cooler. The ultimate reaction mixture was largely freed from unconverted isobutene by distillation and had the composition shown in Table 1, Example 1a.

The conversion of isopropyl alcohol was 64.2%, the isopropyl tert-butyl ether yield 62 mole %, based on the amount of isopropyl alcohol added. The stabilized phase with the composition mentioned above was washed twice with three volumes of water and largely freed of isopropyl alcohol. The ether phase resulting from this water wash had the composition given in Table 1, Example 1b.

EXAMPLE 2

Isobutene and isopropyl alcohol were reacted in a molar ratio of 1.5:1 at a temperature of 40° C. on a strongly acidic ion exchanger resin (commercial product Amberlyst 15). The reactor, filled with catalyst, was fed with 5.2 parts by weight of the specified isopropyl alcohol-isobutene mixture per hour per part by weight of dry catalyst. The other conditions correspond to those given in Example 1. The reaction mixture was distilled to remove most of the unconverted isobutene and had the composition given in Table 1.

EXAMPLE 3

A mixture containing 0.98 mole of water and 1.75 moles of isopropyl alcohol was reacted with isobutene in a molar ratio of water:isopropyl alcohol::isobutene=0.98:1.75:2.60 at a temperature of 50° C. The reactor, filled with catalyst, was fed with 3.8 parts be weight of the specified mixture of water, isopropyl alcohol and isobutene per hour per part by weight of dry catalyst. The other conditions correspond to those given in Example 1. The reaction mixture was distilled to remove most of the unconverted isobutene and had the composition given in Table 1.

TABLE 1

| Components/Example | 1a | 1b | 2 | 3 |
|---|---|---|---|---|
| isobutene | 0.3 | 0.4 | 1.3 | 0.9 |
| isopropyl alcohol | 34.5 | 0.4 | 6.2 | 24.4 |
| tert-butyl alcohol | 0.5 | 0.3 | 1.0 | 30.6 |
| isopropyl tert-butyl ether | 62.7 | 95.7 | 89.6 | 43.1 |
| trimethyl pentene | 1.8 | 2.7 | 1.6 | 0.5 |
| di-isopropyl ether | 0.2 | 0.3 | — | — |
| water | — | 0.2 | <0.1 | 0.4 |

EXAMPLE 4

A hydrocarbon mixture containing isobutene, whose composition is given in Table 2, Column 1, was reacted with a mixture of isopropyl alcohol and sec-butyl alcohol at a temperature of 40° C., whereby a large enough amount of the hydrocarbon fraction containing isobutene was added to make the molar ratio isobutene:isopropyl alcohol:sec-butyl alcohol=1.5:0.5:0.5. The reactor, filled with catalyst (commercial product Lewawit SPC 118), was fed with 5 parts by weight of the mixture containing the hydrocarbon fraction, isopropyl alcohol and sec-butyl alcohol per hour per part by weight of dry catalyst. The other conditions correspond to those in Example 1. The final reaction mixture was freed from most of the unconverted hydrocarbons by distillation and had the composition shown in Table 2, Column 2. The composition of the unconverted hydrocarbons is given in Column 3 of Table 2.

TABLE 2

| Components | % by wt. | % by wt. | % by wt. |
|---|---|---|---|
| propane | 0.4 | — | 0.4 |
| propene | 0.1 | — | 0.1 |
| isobutane | 34.6 | 0.3 | 45.0 |
| n-butane | 15.8 | 0.4 | 19.1 |
| butene-1 | 14.4 | 0.3 | 17.2 |
| isobutene | 34.4 | 0.1 | 17.5 |
| butene-2 | 0.1 | — | 0.1 |
| isopentane | 0.3 | 0.1 | 0.3 |
| isopropyl alcohol | — | 2.9 | — |
| sec-butyl alcohol | — | 6.2 | — |
| tert-butyl alcohol | — | 1.0 | — |
| trimethylpentenes | — | 0.9 | — |
| isopropyl tert-butyl ether | — | 38.8 | — |
| sec-butyl tert-butyl ether | — | 48.7 | — |

It is understood that various modifications and changes in light hereof will be apparent to those skilled in the art and are within the purview of this invention.

What is claimed as new and desired to be secured by Letters Patent of the United States is:

1. A process for producing isopropyl tert-butyl ether from a mixture of light hydrocarbons containing propane and butane comprising:
    (a) separating from said mixture of light hydrocarbons a propane fraction and a butane fraction containing at least n-butane;
    (b) isomerizing at least a portion of said n-butane in said butane fraction from step (a) whereby a hydrocarbon mixture containing at least n-butane and isobutane is formed;
    (c) catalytically dehydrogenating said isobutane in said hydrocarbon mixture from step (b) whereby a hydrocarbon mixture containing at least isobutene is produced;
    (d) catalytically dehydrogenating said propane in said propane fraction from step (a) whereby a hydrocarbon mixture containing at least propene is produced;
    (e) reacting said propene in said hydrocarbon mixture from step (d) with water, whereby a mixture containing hydrocarbons and isopropyl alcohol is formed;
    (f) reacting said isopropyl alcohol from step (e) with at least part of said isobutene in said hydrocarbon mixture from step (c) whereby a mixture containing hydrocarbons and isopropyl tert-butyl ether is formed;

(g) recycling said hydrocarbons in said hydrocarbon mixture from step (e) to step (d);

(h) recycling said hydrocarbons in said hydrocarbon mixture from step (f) to step (c); and (i) recovering at least said isopropyl tert-butyl ether.

2. The process of claim 1 wherein sec-butyl tert-butyl ether is also produced, wherein in step (c) said n-butane is also dehydrogenated whereby said hydrocarbon mixture formed also contains butadiene and n-butenes;

and said hydrocarbon mixture from step (c) is subjected to catalytic hydrogenation and hydroisomerization whereby said butadiene is selectively hydrogenated and butene-1 in said n-butenes is isomerized into butene-2 thereby forming a hydrocarbon mixture containing at least butene-2 and isobutene;

in a step (j) a first portion of said isobutene in said hydrocarbon mixture from step (c) is reacted with isopropyl alcohol to form isopropyl tert-butyl ether;

in a step (k) a second portion of said isobutene in said hydrocarbon mixture from step (c) is reacted with sec-butyl alcohol to form sec-butyl tert-butyl ether;

in a step (l) said butene-2 in said hydrocarbon mixture from step (c) is reacted with water to form sec-butyl alcohol; and at least a portion of said sec-butyl alcohol from step (l) is recycled to react with said isobutene contained in said hydrocarbon mixture from step (c).

3. The process of claim 1 or claim 2 wherein in step (a) said mixture of light hydrocarbons also contains methane and ethane and in step (a) a fraction containing methane and ethane is separated from said mixture of light hydrocarbons;

in steps (c) and (d) methane, ethane and ethene are formed during said dehydrogenation;

said fraction containing methane and ethane is combined with said methane, ethane and ethene formed in said dehydrogenation steps (c) and (d) to form a hydrocarbon mixture which is then catalytically reformed with steam under a pressure of 40-100 bar and at a temperature of 210°-300° C. whereby methyl alcohol is formed; and said methyl alcohol is reacted with a portion of said isobutene from step (c).

4. The process of claim 1 or claim 2, wherein said propane and said butane fractions from step (a) are combined, said combined fractions are dehydrogenated, whereby a hydrocarbon mixture is formed containing $C_3$- and $C_4$-hydrocarbons, and a $C_3$-fraction and a $C_4$-fraction are separated from said hydrocarbon mixture.

5. The process of claim 1 or claim 2 wherein said reaction of step (f) is conducted in the presence of a catalyst at a temperature of 20°-150° C. using 0.5-10 moles of isobutene per 1 mole of isopropyl alcohol.

6. The process of claim 5 wherein said reaction is conducted at a temperature of 30°-60° C.

7. The process of claim 5 wherein said reaction is conducted using 1-3 moles of isobutene per 1 mole of isopropyl alcohol.

8. The process of claim 1 or claim 2 wherein in step (f) only a portion of said isopropyl alcohol is reacted with said isobutene, whereby said mixture formed also contains unreacted isopropyl alcohol, and said unreacted isopropyl alcohol is separated from said product mixture from step (f) by extracting with water.

9. The process of claim 1 or claim 2 wherein in step (f) a mixture of isopropyl alcohol and water is reacted with said isobutene in the presence of an acid catalyst at a temperature of 20°-150° C. using 1-20 moles of isobutene per 1 mole of water and 0.1-10 moles of isobutene per 1 mole of isopropyl alcohol.

10. The process of claim 1 or claim 2 wherein the product mixture of step (e) also contains water and a mixture of isopropyl alcohol and water is separated from said product mixture by rectification, isopropyl alcohol is separated from said mixture of isopropyl alcohol and water by extraction with a mixture of $C_4$-hydrocarbons containing isobutene, whereby an organic phase containing at least isobutene, other $C_4$-hydrocarbons and isopropyl alcohol, and an aqueous phase are formed, said organic phase is separated by distillation into a mixture containing isopropyl alcohol and isobutene and a mixture containing the other $C_4$-hydrocarbons, said mixture containing isopropyl alcohol and isobutene is taken to step (f), said mixture containing other $C_4$-hydrocarbons is recycled to said extraction, and said aqueous phase is recycled to step (e).

11. The process of claim 1 or claim 2 wherein said hydrocarbon mixture from step (b) is divided into a n-butane fraction and an isobutane fraction, said n-butane fraction is recycled to said isomerization step (b), and said isobutane fraction is dehydrogenated in step (c).

12. The process of claim 11 wherein in step (c) only a portion of said isobutane is dehydrogenated whereby said product mixture from step (c) and said product mixture from step (f) contain isobutane, said isobutane in said product mixture from step (f) is separated therefrom and combined with hydrocarbons separated from the product mixture of the hydration step (e) and said isobutane fraction separated from the hydrocarbon mixture of step (b), to form a mixture containing isobutane, which is dehydrogenated in step (c).

13. The process of claim 2 wherein said reaction of sec-butyl alcohol with isobutene is conducted in the presence of a catalyst at a temperature of 20°-150° C. using 0.5-10 moles of isobutene per 1 mole of sec-butyl alcohol.

14. The process of claim 13 wherein said reaction is conducted at a temperature of 30°-60° C.

15. The process of claim 13 wherein said reaction is conducted using 1-3 moles of isobutene per 1 mole of sec-butyl alcohol.

16. The process of claim 2 wherein in step (k) said reaction of isobutene with sec-butyl alcohol is conducted by reacting a mixture of sec-butyl alcohol and water with isobutene at a temperature of 20°-150° C. using 0.1-10 moles of isobutene per 1 mole of sec-butyl alcohol and 1-20 moles of isobutene per 1 mole of water.

17. The process of claim 16 wherein said reaction is conducted at a temperature of 30°-80° C.

18. The process of claim 2 wherein in step (l), a reaction product mixture is formed containing at least sec-butanol, water and hydrocarbons, a sec-butyl alcohol-water mixture is separated from said reaction product mixture by rectification, sec-butyl alcohol is extracted from said sec-butyl alcohol-water mixture by treating with a mixture of C$_4$-hydrocarbons containing isobutene, whereby an organic phase containing at least sec-butyl alcohol, isobutene, and other C$_4$-hydrocarbons, and an aqueous phase are formed, said organic phase is separated by distillation into a mixture containing sec-butyl alcohol and isobutene and a mixture containing the other C$_4$-hydrocarbons, said mixture of sec-butyl alcohol and isobutene is taken to step (k), said mixture containing the other C$_4$-hydrocarbons is recycled to said extraction, and said aqueous phase is recycled to step (l).

19. The process of claim 2 wherein in step (l) reaction product mixture is formed containing at least sec-butanol, water, and hydrocarbons, sec-butyl alcohol is extracted from said reaction product mixture with a hydrocarbon mixture comprising predominantly n-butane and butene-2, whereby an organic phase containing sec-butyl alcohol and hydrocarbons, and an aqueous phase are formed, said organic phase is separated by distillation into a mixture containing at least sec-butanol and a mixture containing the hydrocarbons, said mixture containing sec-butanol is taken to step (k), said hydrocarbons are proportionally recycled to said extraction and to step (l), and said aqueous phase is recycled to step (l).

20. The process of claim 2 wherein isobutene in said hydrocarbon mixture from step (c) is reacted with a mixture of isopropyl alcohol and sec-butyl alcohol.

21. The process of claim 20, wherein said mixture of isopropyl alcohol and sec-butyl alcohol also contains water.

22. The process of claim 3 wherein in step (f) only a portion of said isobutene is reacted whereby said hydrocarbons in said product mixture contain unreacted isobutene, said hydrocarbons are separated from said product mixture and combined with at least a portion of said hydrocarbon mixture from step (c) to form a combined hydrocarbon mixture, and said combined hydrocarbon mixture is reacted with methyl alcohol to form methyl isobutyl ether.

23. The process of claim 2 wherein in step (k) only a portion of said isobutene is reacted, wherein a product mixture is formed containing sec-butyl tert-butyl ether and hydrocarbons including unreacted isobutene, said hydrocarbons including unreacted isobutene are separated from said product mixture and combined with at least a portion of said hydrocarbon mixture from step (c) to form a combined hydrocarbon mixture, and said combined hydrocarbon mixture is reacted with methyl alcohol to form methyl isobutyl ether.

* * * * *